(12) United States Patent
Stock et al.

(10) Patent No.: US 10,087,158 B2
(45) Date of Patent: Oct. 2, 2018

(54) METHOD FOR THE EPOXIDATION OF AN OLEFIN WITH HYDROGEN PEROXIDE

(71) Applicant: Evonik Degussa GmbH, Essen (DE)

(72) Inventors: Jürgen Stock, Frankfurt (DE); Uwe Breitenbach, Gründau (DE); Sebastian Imm, Bad Vilbel (DE); Jürgen Neuroth, Frankfurt (DE); Brigitte Mess, Münster (DE); Matthias Pascaly, Frankfurt (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 15/550,856

(22) PCT Filed: Feb. 3, 2016

(86) PCT No.: PCT/EP2016/052216
§ 371 (c)(1),
(2) Date: Aug. 14, 2017

(87) PCT Pub. No.: WO2016/131649
PCT Pub. Date: Aug. 25, 2016

(65) Prior Publication Data
US 2018/0030011 A1  Feb. 1, 2018

(30) Foreign Application Priority Data
Feb. 17, 2015 (EP) .................................... 15155390

(51) Int. Cl.
*C07D 301/12* (2006.01)

(52) U.S. Cl.
CPC .................. *C07D 301/12* (2013.01)

(58) Field of Classification Search
CPC .................................................. C07D 301/12
See application file for complete search history.

(56) References Cited

U.S. PATENT DOCUMENTS

| | | | |
|---|---|---|---|
| 5,242,602 | A | 9/1993 | Richardson et al. |
| 5,274,140 | A | 12/1993 | Venturello et al. |
| 5,329,024 | A | 7/1994 | Jureller et al. |
| 6,288,248 | B1 | 9/2001 | Strebelle et al. |
| 6,500,311 | B1 | 12/2002 | Sawyer |
| 6,673,950 | B1 | 1/2004 | Teles et al. |
| 6,774,992 | B1 | 8/2004 | Garver et al. |
| 8,802,873 | B2 | 8/2014 | Postma et al. |
| 9,024,048 | B2 | 5/2015 | Kapellen et al. |
| 9,371,300 | B2 | 6/2016 | Kapellen et al. |
| 2002/0004606 | A1 | 1/2002 | Thiele |
| 2003/0171604 | A1 | 9/2003 | Mizuno et al. |
| 2007/0032671 | A1 | 2/2007 | Shinohara et al. |
| 2011/0137054 | A1 | 6/2011 | Postma et al. |
| 2011/0137055 | A1 | 6/2011 | Postma et al. |
| 2012/0289722 | A1 | 11/2012 | Muppa et al. |
| 2014/0113801 | A1 | 4/2014 | Kapellen et al. |
| 2014/0296545 | A1 | 10/2014 | Postma et al. |

FOREIGN PATENT DOCUMENTS

| | | | |
|---|---|---|---|
| EP | 0 559 305 | 9/1993 | |
| EP | 2 537 836 | 12/2012 | |
| WO | WO 2004/028962 | 4/2004 | |
| WO | WO 2004/043941 | 5/2004 | |
| WO | WO 2010/012360 | 2/2010 | |
| WO | WO 2010/012361 | 2/2010 | |
| WO | WO 2010/145901 | 12/2010 | |
| WO | WO 2011/062608 | 5/2011 | |
| WO | WO 2011/063937 | 6/2011 | |
| WO | WO 2011/107188 | 9/2011 | |
| WO | WO 2012/175182 | 12/2012 | |
| WO | WO-2013113578 A1 * | 8/2013 | ........... C07D 301/12 |
| WO | WO 2014/056603 | 4/2014 | |
| WO | WO 2016/131650 | 8/2016 | |
| WO | WO 2016/131652 | 8/2016 | |
| WO | WO 2016/131858 | 8/2016 | |

OTHER PUBLICATIONS

Yang, J.Y., "Catalase and epoxidation activity of manganese salen complexes bearing two xanthene scaffolds." Journal of the American Chemical Society 129.26 (2007): 8192-8198.*
WO-2013113578-A1; WIPO English Machine Translation Dec. 5, 2017.*
Berkessel, A., "Biomimetic Oxidation of Organic Substrates with Hydrogen Peroxide." Contribution, Institut fur Organische Chemie der Universitat zu Koln, Griemstr 4 (2001): 1-11.*
International Search Report for corresponding international application PCT/EP2016/052216 filed Feb. 3, 2016.
Written Opinion of the International Searching Authority for corresponding international application PCT/EP2016/052216 filed Feb. 3, 2016.
International Preliminary Report on Patentability for corresponding international application PCT/EP2016/052216 filed Feb. 3, 2016.
PCT Direct Letter for PCT/EP2016/052216 filed by Applicant during International Stage and mailed Nov. 3, 2015.
International Search Report for related international application PCT/EP2016/052222 filed Feb. 3, 2016.
Written Opinion of the International Searching Authority for related international application PCT/EP2016/052222 filed Feb. 3, 2016.
International Preliminary Report on Patentability for related international application PCT/EP2016/052222 filed Feb. 3, 2016.
PCT Direct Letter for PCT/EP2016/052222 filed by Applicant during International Stage and mailed Jan. 18, 2016.

(Continued)

*Primary Examiner* — John M Mauro
(74) *Attorney, Agent, or Firm* — Law Office of: Michael A. Sanzo, LLC

(57) ABSTRACT

Epoxidation of an olefin is carried out by continuously reacting the olefin with hydrogen peroxide in the presence of a water soluble epoxidation catalyst, comprising a manganese complex, in a reaction mixture comprising an aqueous liquid phase and an organic liquid phase using a loop reactor with mixing of the liquid phases, and during the reaction the concentration of hydrogen peroxide in the aqueous liquid phase is maintained at less than 1.0% by weight.

20 Claims, 1 Drawing Sheet

(56) References Cited

OTHER PUBLICATIONS

European Search Report and Opinion for EP 15 155 418.5 completed Apr. 21, 2015 for international application PCT/ EP2016/052222.
International Search Report for related international application PCT/EP2016/052273 filed Feb. 3, 2016.
Written Opinion of the International Searching Authority for related international application PCT/EP2016/052273 filed Feb. 3, 2016.
International Preliminary Report on Patentability for related international application PCT/EP2016/052273 filed Feb. 3, 2016.
PCT Direct Letter for PCT/EP2016/052273 filed by Applicant during International Stage and mailed Dec. 22, 2015.
European Search Report and Opinion for EP 15155413.6 completed Apr. 23, 2015 for international application PCT/EP2016/052273.
International Search Report for related international application PCT/EP2016/053340 filed Feb. 17, 2016.
Written Opinion of the International Searching Authority for related international application PCT/EP2016/053340 filed Feb. 17, 2016.
International Preliminary Report on Patentability for related international application PCT/EP2016/053340 filed Feb. 17, 2016.
PCT Direct Letter for PCT/EP2016/053340 filed by Applicant during International Stage and mailed Feb. 9, 2016.
De Vos, et al., "Epoxidation of Terminal of Electron-deficient Olefins with $H_2O_2$, catalysed by Mn-trimethyltiazacyclonane Complexes in the Presence of an Oxalate Buffer," *Tetrahedron Letters* 39(20):3221-3224 (May 1998).
U.S. Appl. No. 15/550,836, filed Aug. 14, 2017, Stock.
U.S. Appl. No. 15/550,872, filed Aug. 14, 2017, Stock.
U.S. Appl. No. 15/550,814, filed Aug. 14, 2017, Breitenbach.
Office Action for copending U.S. Appl. No. 15/550,836 dated Dec. 27, 2017.
Office Action for copending U.S. Appl. No. 15/550,872 dated May 18, 2018.
Office Action for copending U.S. Appl. No. 15/550,814 dated Jun. 18, 2018.

\* cited by examiner

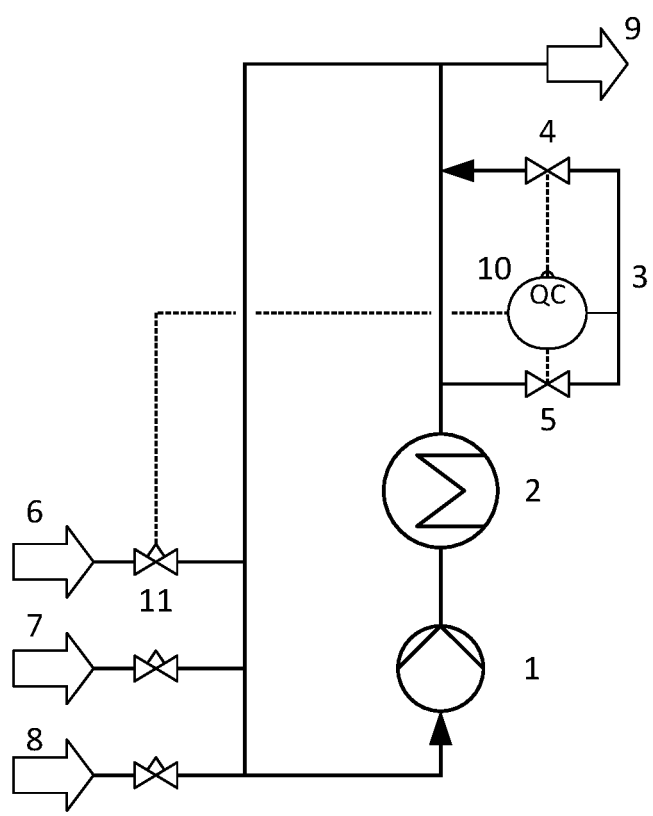

METHOD FOR THE EPOXIDATION OF AN OLEFIN WITH HYDROGEN PEROXIDE

CROSS REFERENCE TO RELATED APPLICATIONS

The present application is US national stage of international application PCT/EP2016/052216, which had an international filing date of Feb. 3, 2016, and which was published in English under PCT Article 21(2) on Aug. 25, 2016. The application claims priority to European application 15155390.6, filed on Feb. 17, 2015.

FIELD OF THE INVENTION

The invention relates to a method for the epoxidation of an olefin with hydrogen peroxide in the presence of a water soluble epoxidation catalyst comprising a manganese complex where the reaction is carried out in a reaction mixture comprising an aqueous liquid phase and an organic liquid phase.

BACKGROUND OF THE INVENTION

Methods for the epoxidation of an olefin with hydrogen peroxide using a water soluble manganese complex as epoxidation catalyst are known from D. E. De Vos et al., Tetrahedron Letters 39 (1998) 3221-3224 and from U.S. Pat. No. 5,329,024. WO 2010/012361 teaches to carry out the epoxidation in a biphasic system comprising an organic phase and an aqueous phase. WO 2010/012361 also suggests to add hydrogen peroxide at a rate about equal to the reaction rate of the catalytic epoxidation to ensure optimal peroxide efficiency.

WO 2011/107188 discloses use of a loop reactor for epoxidation with this catalyst in a multiphasic reaction mixture comprising an organic phase and an aqueous phase.

WO 2014/056603 discloses epoxidation with this catalyst in the presence of alkaline earth metal ions and suggests providing the oxidant at a concentration of from 0.05 to 4% by weight. In the examples, epoxidation is carried out in batch in a stirred vessel with a variable hydrogen peroxide feed aiming at a concentration of 0.1% by weight.

U.S. Pat. No. 6,774,992 discloses measuring the concentration of hydrogen peroxide in the aqueous phase of a pulp bleaching effluent. Raman intensities are measured at different wavenumbers to additionally determine amounts of further species present in the aqueous phase.

SUMMARY OF THE INVENTION

It has now been found that for epoxidation in a reaction mixture comprising two liquid phases the decomposition of hydrogen peroxide during epoxidation depends strongly on the hydrogen peroxide concentration in the aqueous phase. Maintaining the concentration of hydrogen peroxide in the aqueous phase at less than 1.0% by weight, preferably less than 0.7% by weight, considerably reduces decomposition of hydrogen peroxide and oxygen formation.

It has further been found that determining the concentration of hydrogen peroxide in the aqueous phase of a continuously operated epoxidation reaction is difficult, as the concentration rapidly changes in samples withdrawn from the reaction mixture. A reliable measurement of hydrogen peroxide concentration is possible by inline measurement when the measuring device is arranged in a measuring section where the liquid phases of the reaction mixture are temporarily separated and the measuring device is in contact with the separated aqueous phase. Measuring is preferably by spectroscopy, in particular by Raman spectroscopy.

Subject of the invention is therefore a method for the epoxidation of an olefin, comprising continuously reacting the olefin with hydrogen peroxide in the presence of a water soluble epoxidation catalyst, comprising a manganese complex, the reaction being carried out in a reaction mixture comprising an aqueous liquid phase and an organic liquid phase using a loop reactor with mixing of the liquid phases, wherein during the reaction the concentration of hydrogen peroxide in the aqueous liquid phase is maintained at less than 1.0% by weight.

Preferably, the loop reactor comprises a measuring section, in which the liquid phases are temporarily separated into a separated aqueous phase and a separated organic phase by lowering the flow rate. A measuring device is arranged in the measuring section in contact with the separated aqueous phase, and the concentration of hydrogen peroxide in the separated aqueous phase is determined with this measuring device.

BRIEF DESCRIPTION OF DRAWINGS

The FIGURE on page 1/1 shows a preferred embodiment of the method of the invention with a measuring section in a side stream blocked off by two valves.

DETAILED DESCRIPTION OF THE INVENTION

In the method of the invention an olefin is reacted with hydrogen peroxide in the presence of a water soluble epoxidation catalyst in a reaction mixture comprising an aqueous liquid phase and an organic liquid phase.

The olefin may contain one or several carbon-carbon double bonds. In olefins containing two or more double bonds, the double bonds may be isolated or conjugated, isolated double bonds being preferred. The olefin may be linear, branched or cyclic and may carry substituents, in particular one or more substituents selected from aryl groups, halogens, free and esterified hydroxyl groups, alkoxy groups and carboxyl groups. The substituents may be in vinylic or allylic position or bonded to another position of the olefin, with substituents in allylic position being preferred.

The olefin preferably has a solubility in water of from 0.01 g/L to 100 g/L at 20° C., more preferably of from 0.01 g/L to 10 g/L at 20° C., in order to achieve both a high rate of reaction in epoxidation and formation of an organic liquid phase without addition of solvent.

In a preferred embodiment, the olefin is allyl chloride and the method of the invention provides epichlorohydrin as the reaction product. In another preferred embodiment, the olefin is propene and the method of the invention provides propene oxide as the reaction product.

Hydrogen peroxide can be used as an aqueous solution, preferably containing from 20 to 75% by weight hydrogen peroxide and most preferably from 40 to 70% by weight. Preferably, an aqueous hydrogen peroxide solution prepared by an anthraquinone process is used. A crude hydrogen peroxide solution as obtained in the extraction step of the anthraquinone process may be used in the method of the invention.

The water soluble epoxidation catalyst comprises a manganese complex. The manganese complex preferably comprises at least one polydentate ligand which preferably coordinates through nitrogen atoms, most preferably through tertiary amino groups. The manganese complex may be a mononuclear complex of formula $[LMnX_m]Y_n$, a dinuclear complex of formula $[LMn(\mu-X)_mMnL]Y_n$ or a polynuclear complex of formula $[L_pMn_p(\mu-X)_m]Y_n$, where L is a polydentate ligand, X is a coordinating species, $\mu$-X is a bridging coordinating species, Y is a non-coordinating counter ion, m is 1, 2 or 3, n is an integer providing for the charge neutrality of the complex, and p is from 3 to 5. X and $\mu$-X are preferably selected from the group consisting of $RO^-$, $Cl^-$, $Br^-$, $I^-$, $F^-$, $NCS^-$, $N_3^-$, $I_3^-$, $NH_3$, $NR_3$, $RCOO^-$, $RSO_3^-$, $ROSO_3^-$, $OH^-$, $O^{2-}$, $O_2^{2-}$, $HOO^-$, $H_2O$, $SH^-$, $CN^-$, $OCN^-$, $C_2O_4^{2-}$ and $SO_4^{2-}$, where R is alkyl, cycloalkyl, aryl or aralkyl with no more than 20 carbon atoms. Y is preferably selected from the group consisting of $RO^-$, $Cl^-$, $Br^-$, $I^-$, $F^-$, $RCOO—$, $SO_4^{2-}$, $PF_6^-$, p-tolylsulfonate and trifluoromethylsulfonate, where R is alkyl, cycloalkyl, aryl or aralkyl with no more than 20 carbon atoms. Manganese may be in the oxidation state +2, +3, +4, or +7, the oxidation states +3 and +4 being preferred.

Preferred polydentate ligands are acyclic polyamines containing at least 7 atoms in the backbone or cyclic polyamines containing at least 9 atoms in the ring, each having the nitrogen atoms separated by at least two carbon atoms. Most preferred are ligands having a 1,4,7-triazacyclononane (Tacn) ring system, which may be substituted with one or more alkyl, cycloalkyl, aryl or aralkyl groups each containing up to 20 carbon atoms. Preferred substituents are methyl groups. Suitable ligands with a Tacn ring system are N',N'',N'''-trimethyl-1,4,7-triazacyclononane (TmTacn) and 2-methyl-1,4,7-trimethyl-1,4,7-triazacyclononane, with TmTacn being preferred. Another suitable ligand is 1,5,9-trimethyl-1,5,9-triazacyclododecane.

Most preferred are the dinuclear manganese complexes $[(TmTacn)Mn^{IV}(\mu-O)_3Mn^{IV}(TmTacn)](PF_6)_2$ and $[(TmTacn)Mn^{IV}(\mu-O)_3Mn^{IV}(TmTacn)](CH_3COO)_2$.

The manganese complex may be formed in the reaction mixture by reaction of the polydentate ligand with a manganese salt, preferably manganese sulfate, manganese acetate, manganese nitrate, manganese chloride or manganese bromide with $Mn^{2+}$ or $Mn^{3+}$. Preferably, the manganese complex is prepared separately and added to the reaction mixture.

The water soluble epoxidation catalyst preferably comprises oxalic acid, an oxalate or a mixture of both as a co-catalyst in addition to the manganese complex. The co-catalyst is preferably used in a molar excess to the manganese complex, preferably with a molar ratio of co-catalyst to manganese complex in the range of from 10:1 to 10 000:1.

The reaction is carried out in a reaction mixture comprising an aqueous liquid phase and an organic liquid phase with mixing of the liquid phases. Preferably, the ratio of the volume of the aqueous phase to the volume of the organic phase is maintained in the range of from 10:1 to 1:10, more preferably from 2:1 to 1:4. Mixing of the liquid phases can be performed by turbulent flow of the reaction mixture, by passing reaction mixture through fixed mixing elements, such as static mixers, structured packings or random packings, or by a moving mixing element, such as a stirrer or a rotating pump.

The aqueous phase preferably comprises less than 30% by weight, more preferably less than 5% by weight of a solvent. The organic phase may contain a water insoluble solvent, but preferably contains less than 30% by weight, more preferably less than 5% by weight of a solvent. In both instances the term solvent refers to compounds added in addition to olefin, epoxidation catalyst, co-catalyst and impurities introduced with these components, and does not encompass products formed from the olefin.

The epoxidation reaction is preferably carried out at a temperature of from 0° C. to 70° C., more preferably from 5° C. to 40° C. and most preferably from 10° C. to 30° C. When the boiling point of the olefin at 1 bar is close to or higher than the reaction temperature, the epoxidation is carried out at elevated pressure to maintain the olefin in the liquid phase. When the olefin is propene, the epoxidation reaction is preferably carried out at a pressure of from 0.8 to 2.0 MPa. When the olefin is allyl chloride, the epoxidation reaction is preferably carried out at a pressure of from 0.12 to 1.0 MPa.

The reaction is carried out continuously in a loop reactor. The term loop reactor here refers to a reactor in which reaction mixture is circulated driven by a pump. Pumping of the reaction mixture provides mixing of the liquid phases. The loop reactor may comprise vessels for increasing the volume in the loop and providing the residence time necessary for achieving the desired hydrogen peroxide conversion. Preferably, further mixing of the reaction mixture is provided in such vessels, for example by static mixers, structured packings or random packings arranged in a tube of enlarged diameter or by a stirred vessel arranged in the reactor loop. Preferably, a heat exchanger is arranged in the loop for cooling the reaction mixture in order to remove the heat of reaction, the reaction mixture preferably being passed through the heat exchanger in every cycle of the loop. The heat exchanger is preferably a tube bundle heat exchanger with the reaction mixture being passed through the tubes or a plate heat exchanger. The diameter of the tubes or the distance between plates is preferably chosen sufficiently narrow for providing turbulent flow and mixing of the two liquid phases.

The average residence time in the loop reactor, calculated as the ratio of the volume of the loop reactor divided by the sum of all fluid flows entering the loop reactor, is preferably selected to provide a hydrogen peroxide conversion of more than 85%, more preferably of from 95% to 99.5%. For this purpose, the average residence time is preferably from 20 to 240 min.

During the reaction, the pH of the aqueous phase is preferably maintained in the range of from 2 to 6, more preferably 2.5 to 5. Preferably, a buffer is added to stabilize the pH in this range. The buffer may be an inorganic buffer, such as a phosphate buffer, or preferably an organic buffer, such as a carboxylic acid/carboxylate buffer. Most preferably, an oxalic acid/oxalate buffer is used, which acts both as buffer and as co-catalyst. The buffer may be prepared previous to feeding it to the loop reactor or may be preferably generated within the loop reactor by separately feeding an acid and a base to the loop reactor. More preferably, aqueous solutions of oxalic acid and sodium hydroxide are fed separately to the loop reactor and most preferably the solution of oxalic acid is fed at an essentially constant rate and the feeding of the sodium hydroxide solution is adjusted to maintain the pH in the desired range.

The olefin is preferably used in molar excess to hydrogen peroxide in order to achieve high conversion of hydrogen peroxide and the molar ratio of olefin fed to the loop reactor to hydrogen peroxide fed to the loop reactor is preferably from 1.2:1 to 12:1, more preferably from 2:1 to 8:1. The amount of catalyst fed to the loop reactor is preferably chosen to provide a molar ratio of hydrogen peroxide fed to the loop reactor to manganese fed to the loop reactor of from 100:1 to 10 000 000:1, more preferably from 1000:1 to 1 000 000:1 and most preferably 10 000:1 to 100 000:1.

In the method of the invention the concentration of hydrogen peroxide in the aqueous liquid phase is maintained at less than 1.0% by weight during the reaction. Preferably, the concentration of hydrogen peroxide is maintained at from 0.1 to 0.7% by weight, more preferably from 0.2 to 0.5% by weight. The concentration of hydrogen peroxide in the aqueous liquid phase may be adjusted by adjusting the molar ratio of olefin to hydrogen peroxide fed to the loop reactor, adjusting the feed rate for feeding hydrogen peroxide to the loop reactor or adjusting the feed rate for feeding epoxidation catalyst to the reactor, with a higher molar ratio of olefin to hydrogen peroxide, a lower feed rate for hydrogen peroxide or a higher feed rate for epoxidation catalyst leading to a lower concentration of hydrogen peroxide in the aqueous liquid phase.

The concentration of hydrogen peroxide in the aqueous liquid phase may be measured with any method known from the prior art. However, since the concentration of hydrogen peroxide rapidly changes in samples of aqueous liquid phase withdrawn from a loop reactor, the concentration of hydrogen peroxide is preferably measured online and more preferably measured inline. The term online here denotes a measurement carried out with a measuring device attached to the loop reactor on a sample of aqueous liquid phase withdrawn from the reaction loop and the term inline denotes a measurement carried out on aqueous liquid phase circulating in the reaction loop.

In a preferred embodiment of the method of the invention, the loop reactor comprises a measuring section, in which the liquid phases are temporarily separated into a separated aqueous phase and a separated organic phase. A measuring device is arranged in the measuring section in contact with the separated aqueous phase, and the concentration of hydrogen peroxide in the separated aqueous phase is determined with this measuring device.

The measuring section may be located in the main loop of the loop reactor, but is preferably located in a side stream to the loop reactor. The term side stream here refers to a stream which is continuously withdrawn from the loop reactor and is at least partially returned to the loop reactor. Preferably, the entire side stream is returned to the loop reactor. Flow rate in the side stream may be adjusted independently of the flow rate in the main loop, for example by a pump or by a valve in the side stream.

The liquid phases can be temporarily separated by settling or by centrifugal force and are preferably separated by lowering the flow rate which leads to settling. In a preferred embodiment, the flow rate is lowered in the measuring section by enlarging the flow cross section. Preferably, a side stream is passed through a horizontal pipe having a section with an enlarged diameter where lowering of the flow rate leads to temporary phase separation by settling. In another preferred embodiment, the measuring section is located in a side stream and a valve is used for lowering the flow rate or temporarily stopping the flow in the measuring section.

In principle, any device known from the prior art for measuring the concentration of hydrogen peroxide in an aqueous solution, may be used as measuring device in the measuring section. Examples of such devices are amperometric sensors operating by electrochemical reduction or oxidation of hydrogen peroxide or online titration analyzers operating on samples withdrawn from the separated aqueous phase. Preferably, a device is used which measures the concentration of hydrogen peroxide by spectroscopy. Spectroscopic measurement may be by infrared spectroscopy, near infrared spectroscopy, UV spectroscopy or Raman spectroscopy, with Raman spectroscopy being preferred. Most preferably, the concentration of hydrogen peroxide is measured by Raman spectroscopy in a measuring section located in a side stream to the loop reactor and the measuring section is blocked off by two valves during measurement of the hydrogen peroxide concentration. Blocking off the measuring section improves safety of the process and prevents that ignition of a flammable mixture in the measuring section by the laser used for Raman spectroscopy may propagate into the main reaction loop.

Preferably, an IR laser, preferably operating at a wavelength of 785 nm, is used for measuring the concentration of hydrogen peroxide by Raman spectroscopy in order to minimize interferences from fluorescence. The concentration of hydrogen peroxide is preferably determined from the intensity of the Raman peak at 786 $cm^{-1}$. Interference from Raman peaks of dissolved olefin and olefin oxide is preferably compensated by additionally measuring the intensity of Raman peaks characteristic for the olefin and olefin oxide, such as the peak at 1646 $cm^{-1}$ characteristic for propene and the peak at 730 $cm^{-1}$ characteristic for propene oxide, using linear combination or chemometric methods, such as known from U.S. Pat. No. 5,242,602 and U.S. Pat. No. 6,774,992. Calibration for simultaneous measurement of concentrations of hydrogen peroxide, olefin and olefin oxide by Raman spectroscopy can be carried out with commercial software, for example with PLS/Plus IQ™ from Thermo Scientific. Additional measurement of the concentration of the olefin in the aqueous phase by Raman spectroscopy also allows to monitor phase transfer of the olefin to the aqueous phase and to adjust the intensity of mixing in the loop reactor in order to overcome phase transfer limitation.

Preferably, the addition of hydrogen peroxide and/or addition of epoxidation catalyst to the loop reactor are controlled based on the determined concentration of hydrogen peroxide. More preferably, the addition of epoxidation catalyst is controlled to maintain an essentially constant concentration of hydrogen peroxide. Most preferably, this is done at a constant feed rate of hydrogen peroxide in order to achieve stationary continuous operation of the epoxidation reaction with little hydrogen peroxide decomposition.

In another preferred embodiment, the feeding of hydrogen peroxide to the loop reactor is stopped when the measured hydrogen peroxide concentration exceeds a preset safety limit, in order to limit the hydrogen peroxide holdup of the loop reactor and thereby prevent the danger of a runaway reaction in the loop reactor.

The FIGURE on page 1/1 shows a preferred embodiment of the method of the invention with a measuring section in a side stream blocked off by two valves.

The FIGURE on page 1/1 shows a loop reactor comprising a circulation pump (1), a heat exchanger (2) for cooling the reaction mixture and a measuring section (3) located in a side stream to the loop reactor which can be blocked off by two valves (4, 5). Catalyst (6), hydrogen peroxide (7) and olefin (8) are fed to the loop reactor. Buffer and co-catalyst can also be fed to the loop reactor, but are not shown. An amount of reaction mixture corresponding to the feed is withdrawn as a product stream (9), comprising olefin oxide formed by the reaction, along with non-reacted olefin and hydrogen peroxide, water formed from and introduced with the hydrogen peroxide and optional additives, such as buffer and co-catalyst. The reaction mixture is circulated in the loop by pump (1) with a side stream passing through measuring section (3) when valves (4, 5) are open. A measuring device (10) comprising a Raman spectrometer is arranged in measuring section (3) at a position where it is in contact with the aqueous phase when phase separation occurs in the measuring section. The hydrogen peroxide concentration is measured intermittently by closing valves (4, 5), letting the reaction mixture settle in measuring section (3) during a dwell time to separate the reaction mixture enclosed between the valves into a separated aqueous phase and a separated organic phase, measuring the concentration of hydrogen peroxide in the separated aqueous phase with the Raman spectrometer after the dwell time and reopening valves (4, 5) after this measurement to return the separated phases to the main loop and re-establish the side stream. Closing and opening of the valves is operated by the measuring device (10), which also controls a valve (11) for adjusting dosage of the catalyst (6) based on the measured concentration of hydrogen peroxide, increasing catalyst dosage when the concentration of hydrogen peroxide is higher than the desired value and decreasing catalyst dosage when the concentration of hydrogen peroxide is lower than the desired value.

LIST OF REFERENCE SIGNS

1 Circulation pump
2 Heat exchanger
3 Measuring section
4 Valve
5 Valve
6 Catalyst
7 Hydrogen peroxide
8 Olefin
9 Product stream
10 Measuring device comprising a Raman spectrometer
11 Valve

EXAMPLES

General

Continuous epoxidation of propene was carried out in a loop reactor constructed from steel tubes with a cooling mantle and static mixers arranged within the tubes. The loop reactor comprised in series feed lines for starting materials, two circulation pumps, and a withdrawal line for reaction mixture. The withdrawal line for reaction mixture was connected to phase separators for separating withdrawn reaction mixture into a liquid aqueous phase, a liquid organic phase and a gas phase. Nitrogen was introduced into the second phase separator and gas phase was withdrawn with a pressure regulating valve to maintain a constant pressure of from 1.45 to 1.50 MPa. The loop of the loop reactor had a total volume of 1200 ml and was operated at a circulation rate of 100 kg/h. The loop reactor also comprised a measuring section in a side stream by-passing the second group of tube reactors, comprising optical windows for Raman spectroscopic measurement and two blocking valves downstream and upstream of the optical window.

Epoxidations were carried out at 14 to 15° C. with separate feeding of an aqueous catalyst solution containing [(TmTacn)Mn$^{IV}$(μ-O)$_3$Mn$^{IV}$(TmTacn)](CH$_3$COO)$_2$ as catalyst, an aqueous solution of an oxalic acid/sodium oxalate buffer, an aqueous hydrogen peroxide solution and liquid propene. The pH of the aqueous phase of the reaction mixture was maintained in the range of 4.1 to 4.3 by adding small amounts of a sodium hydroxide solution if needed.

Aqueous phase, organic phase and gas phase were analyzed for propene oxide by GC. Hydrogen peroxide decomposition was determined by measuring the flow rate of the gas phase and a paramagnetic measurement of the oxygen content of the gas phase. The hydrogen peroxide concentration in the aqueous phase of the reaction mixture was measured on-line by closing the blocking valves in the side stream, waiting 10 s for phase separation and Raman spectroscopic determination of the hydrogen peroxide content of the separated aqueous phase, followed by reopening the blocking valves. Raman spectra were taken at a wavelength of 785 nm, determining the concentration of hydrogen peroxide from the intensity of the Raman peak at 786 cm$^{-1}$ with corrections for interference from propene and propene oxide based on the intensity of the Raman peaks at 1646 cm$^{-1}$ and 730 cm$^{-1}$. Off-line measurements of hydrogen peroxide concentration were carried out by withdrawing a sample of the two phase reaction mixture, pressure release of the sample with outgassing of propene, waiting for separation of organic phase and aqueous phase and cerimetric titration of hydrogen peroxide in an aliquot of the aqueous phase, where the time span from withdrawing the sample to the endpoint of the titration was approximately 2 min.

Examples 1 to 4

Examples 1 to 4 were carried out varying the hydrogen peroxide concentration in the feed. The combined feed rate of catalyst solution, buffer solution and hydrogen peroxide solution was 570 g/h, feeding 0.122 mmol/h of catalyst, 17.9 mmol/h of oxalic acid, 16.8 mmol/h of sodium oxalate, and the amounts of hydrogen peroxide given in table 1. Propene was fed at a rate of 546 g/h. The hydrogen peroxide concentration measured by Raman spectroscopy, the propene oxide yield (based on hydrogen peroxide charged) and the fraction of hydrogen peroxide decomposed to oxygen are given in table 1.

TABLE 1

| Example | H$_2$O$_2$ fed in mol/h | H$_2$O$_2$ concentration in % by weight | Propene oxide yield in % | H$_2$O$_2$ decomposed to oxygen in % |
|---|---|---|---|---|
| 1 | 2.32 | 0.55 | 74 | 0.3 |
| 2 | 2.86 | 0.7 | 72 | 2.3 |
| 3 | 3.47 | 2.2 | 49 | 31 |
| 4 | 4.02 | 3.5 | 41 | 39 |

Examples 5 and 6

Examples 5 and 6 were carried out with identical feed rates and concentrations of aqueous feed solutions, varying the feed rate of propene. 120 g/h of a 0.063% by weight catalyst solution, 228 g/h of a buffer solution containing 1% by weight oxalic acid dihydrate and 1% by weight sodium oxalate, and 330 g/h of a 30% by weight hydrogen peroxide solution were fed in both examples. The propene feed rate was 546 g/h in example 6 and 336 g/h in example 7. The hydrogen peroxide concentrations measured on-line by Raman spectroscopy and off-line by cerimetric titration, the propene oxide yield (based on hydrogen peroxide charged) and the fraction of hydrogen peroxide decomposed to oxygen are given in table 2.

TABLE 2

| Example | H$_2$O$_2$ concentration by in-line Raman in % by weight | H$_2$O$_2$ concentration by off-line titration in % by weight | Propene oxide yield in % | H$_2$O$_2$ decomposed oxygen to in % |
|---|---|---|---|---|
| 5 | 0.7 | 0.02 | 73 | 2.2 |
| 6 | 1.6 | 0.06 | 63 | 13 |

The examples demonstrate that decomposition of hydrogen peroxide increases sharply with the concentration of hydrogen peroxide in the aqueous phase of the reaction mixture and that low levels of hydrogen peroxide decomposition can be achieved by maintaining a concentration of hydrogen peroxide of less than 1% by weight. Examples 5 and 6 also demonstrate that an off-line measurement of a withdrawn sample provides erroneously low values for hydrogen peroxide concentration that cannot be used for controlling the hydrogen peroxide concentration in the reaction mixture, whereas an in-line measurement with temporary phase separation allows a more precise measurement of the hydrogen peroxide concentration in the aqueous phase of the reaction mixture.

The invention claimed is:

1. A method for the epoxidation of an olefin, comprising continuously reacting the olefin with hydrogen peroxide in the presence of a water soluble epoxidation catalyst, comprising a manganese complex, wherein said manganese complex comprises at least one ligand having a 1,4,7-triazacyclononane ring system, and wherein:
   a) the reaction is carried out in a reaction mixture comprising an aqueous liquid phase and an organic liquid phase using a loop reactor with mixing of the liquid phases;
   b) during the reaction, the concentration of hydrogen peroxide in the aqueous liquid phase is maintained at less than 1.0% by weight.

2. The method of claim 1, wherein:
   a) the loop reactor comprises a measuring section within the loop, in which the liquid phases are temporarily separated into a separated aqueous phase and a separated organic phase;
   b) a measuring device is arranged in the measuring section in contact with the separated aqueous phase; and
   c) the concentration of hydrogen peroxide in the separated aqueous phase is determined with said measuring device.

3. The method of claim 2, wherein the liquid phases are temporarily separated by lowering the flow rate.

4. The method of claim 3, wherein the flow rate is lowered in the measuring section by enlarging the flow cross section.

5. The method of claim 2, wherein the measuring section is located in a side stream to the loop reactor.

6. The method of claim 5, wherein a valve is used for lowering the flow rate or temporarily stopping the flow in the measuring section.

7. The method of claim 2, wherein the concentration of hydrogen peroxide is measured by spectroscopy.

8. The method of claim 7, wherein the concentration of hydrogen peroxide is measured by Raman spectroscopy.

9. The method of claim 8, wherein the measuring section is located in a side stream to the loop reactor and is blocked off by two valves during measurement of the hydrogen peroxide concentration.

10. The method of claim 2, wherein addition of hydrogen peroxide to the loop reactor, addition of epoxidation catalyst to the loop reactor, or both are controlled based on the determined concentration of hydrogen peroxide.

11. The method of claim 10, wherein addition of epoxidation catalyst is controlled to maintain an essentially constant concentration of hydrogen peroxide.

12. The method of claim 1, wherein the olefin is propene or allyl chloride.

13. The method of claim 1, wherein the manganese complex comprises a 1,4,7-trimethyl-1,4,7-triazacyclonane ligand.

14. The method of claim 13, wherein the reaction is carried out in the presence of an oxalate buffer.

15. The method of claim 13, wherein during the reaction the pH of the aqueous liquid phase is maintained in the range from 2.5 to 5.

16. A method for the epoxidation of allyl chloride, comprising continuously reacting allyl chloride with hydrogen peroxide in the presence of an oxalate buffer and a water soluble epoxidation catalyst comprising a manganese complex with a 1,4,7-trimethyl-1,4,7-triazacyclonane ligand; wherein:
   a) the reaction is carried out in a reaction mixture comprising an aqueous liquid phase and an organic liquid phase using a loop reactor with mixing of the liquid phases;
   b) the loop reactor comprises a measuring section within the loop, in which the liquid phases are temporarily separated into a separated aqueous phase and a separated organic phase;
   c) a measuring device is arranged in the measuring section in contact with the separated aqueous phase;
   d) the concentration of hydrogen peroxide in the separated aqueous phase is determined with said measuring device; and
   e) during the reaction the concentration of hydrogen peroxide in the aqueous liquid phase is maintained at less than 1.0% by weight.

17. The method of claim 16, wherein the measuring section is located in a side stream to the loop reactor.

18. The method of claim 17, wherein the concentration of hydrogen peroxide is measured by Raman spectroscopy and the measuring section is blocked off by two valves during measurement of the hydrogen peroxide concentration.

19. The method of claim 16, wherein addition of epoxidation catalyst to the loop reactor is controlled to maintain an essentially constant concentration of hydrogen peroxide.

20. The method of claim 16, wherein the molar ratio of allyl chloride fed to the loop reactor to hydrogen peroxide fed to the loop reactor is from 1.2:1 to 12:1.

* * * * *